(12) United States Patent
Deno et al.

(10) Patent No.: US 12,073,925 B2
(45) Date of Patent: Aug. 27, 2024

(54) MEDICAL QUESTIONNAIRE CREATION ASSIST DEVICE, METHOD, AND NON-TRANSITORY COMPUTER-READABLE STORAGE MEDIUM STORING PROGRAM

(71) Applicant: OMRON HEALTHCARE Co., Ltd., Kyoto (JP)

(72) Inventors: Toru Deno, Kyoto (JP); Naoki Tsuchiya, Kyoto (JP); Takahiro Hamaguchi, Kyoto (JP); Yasushi Matsuoka, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 430 days.

(21) Appl. No.: 17/145,720

(22) Filed: Jan. 11, 2021

(65) Prior Publication Data

US 2021/0134403 A1 May 6, 2021

Related U.S. Application Data

(63) Continuation of application No. PCT/JP2019/026069, filed on Jul. 1, 2019.

(30) Foreign Application Priority Data

Jul. 17, 2018 (JP) ................. 2018-134034

(51) Int. Cl.
*G16H 10/20* (2018.01)
*G06F 3/0482* (2013.01)
(Continued)

(52) U.S. Cl.
CPC ........... *G16H 10/20* (2018.01); *G06F 3/0482* (2013.01); *G06F 40/186* (2020.01); *G16H 10/60* (2018.01)

(58) Field of Classification Search
CPC ........ G16H 10/20; G16H 10/60; G16H 40/67; G16H 80/00; G06F 40/174; G06F 3/0482; G06F 40/186
(Continued)

(56) References Cited

U.S. PATENT DOCUMENTS

| 10,199,123 B2* | 2/2019 | Hussam | G06Q 10/06 |
| 2002/0022975 A1* | 2/2002 | Blasingame | G16H 10/20 |
| | | | 705/3 |

(Continued)

FOREIGN PATENT DOCUMENTS

| CN | 1902650 A | 1/2007 |
| EP | 1865432 A2 | 12/2007 |

(Continued)

OTHER PUBLICATIONS 1741-7015-12-109.pdf—"Adaptation and validation of the Treatment Burden Questionnaire (TBQ) in English using an internet platform", Research Article by Viet-Thi Tran, Magdalena Harrington, Victor M Montori, Caroline Barnes, Paul Wicks and Philippe Ravaud, BioMed Central, BMC Medicine, Feb. 2014, 12:109 (Year: 2014).*

(Continued)

*Primary Examiner* — Christopher B Tokarczyk
*Assistant Examiner* — Teresa S Williams
(74) *Attorney, Agent, or Firm* — Birch, Stewart, Kolasch & Birch, LLP

(57) ABSTRACT

When creating a medical questionnaire of a patient, a medical questionnaire creation assist terminal acquires past clinical data of the patient from an EMR server or an EHR server on the basis of medical questionnaire template data, and also acquires PHR data from a mobile information terminal of the patient to create medical questionnaire basic data. Then, the medical questionnaire creation assist termi- (Continued)

nal creates medical questionnaire completed data by adding medical interview statement information manually input by the patient or medical staff to incomplete items in the medical questionnaire basic data, and notifies a physician terminal of the medical questionnaire completed data.

16 Claims, 6 Drawing Sheets

(51) Int. Cl.
  *G06F 40/186* (2020.01)
  *G16H 10/60* (2018.01)
(58) Field of Classification Search
  USPC .............................................................. 705/3
  See application file for complete search history.

(56) References Cited

U.S. PATENT DOCUMENTS

| 2007/0106535 | A1 | 5/2007 | Matsunaga |
| 2007/0299696 | A1 | 12/2007 | Matsubara et al. |
| 2014/0298165 | A1 | 10/2014 | Hussam |

FOREIGN PATENT DOCUMENTS

| JP | H11-306261 | A | 11/1999 |
| JP | 2002-366655 | A | 12/2002 |
| JP | 2003-122846 | A | 4/2003 |
| JP | 2005-122380 | A | 5/2005 |
| JP | 2007-328740 | A | 12/2007 |
| JP | 2008-197742 | A | 8/2008 |
| JP | 2011-103056 | A | 5/2011 |
| WO | WO-2023201285 | A2 * | 10/2023 |

OTHER PUBLICATIONS

English translation of International Preliminary Report on Patentability mailed Jan. 21, 2021, in PCT/JP2019/026069.
Japanese Notice of Reasons for Refusal for Japanese Application No. 2018-134034, dated Sep. 20, 2022, with English translation.
Chinese Office Action and Search Report for Chinese Application No. 201980040538.6, dated Oct. 23, 2023.
Chinese Office Action and Search Report for Chinese Application No. 201980040538.6, dated Jun. 6, 2024, with English translation.

* cited by examiner

HOSPITAL NAME _____

DATE _____ (MONTH/DAY/YEAR)

TO INTERNAL MEDICINE OUTPATIENTS

A1 { FURIGANA
NAME               ☐MALE ☐FEMALE   AGE (YEARS)/ CONSULTATION CARD
                                               REGISTRATION NUMBER

B1 { BLOOD PRESSURE      / HEIGHT   cm  / WEIGHT   kg  / BODY TEMPERATURE TODAY   °C

C {
- ■ PLEASE SPECIFY YOUR MEDICAL PROBLEM OR SYMPTOMS.
  WHAT PART OF YOUR BODY IS WRONG AND HOW?
- ■ WHEN DID THE SYMPTOMS START?

A2 {
- ■ HAVE YOU VISITED ANY DOCTOR OFFICE OR HOSPITAL FOR YOUR CURRENT SYMPTOMS?
  ☐ NO    ☐ YES  I AM RECEIVING MEDICAL TREATMENT AT _____ SINCE _____ (MONTH/DAY/YEAR).
- ■ PLEASE ENTER A CHECK MARK TO ANY ILLNESS YOU HAVE HAD BEFORE OR TO WHICH YOU ARE UNDERGOING TREATMENT, AND ENTER WHEN INSIDE THE PARENTHESES.
  ☐ ASTHMA       ( AROUND )  ☐ PNEUMONIA    ( AROUND )  ☐ TUBERCULOSIS ( AROUND )
  ☐ HYPERTENSION ( AROUND )  ☐ LIVER DISEASE ( AROUND ) ☐ KIDNEY DISEASE ( AROUND )
  ☐ DIABETES     ( AROUND )  ☐ STROKE       ( AROUND )  ☐ CANCER       ( AROUND )
  ☐ HEART DISEASE ( AROUND ) ☐ OTHER    ( DISEASE NAME:                          )
- ■ HAVE YOU HAD ANY SURGERIES IN THE PAST?
  ☐ NO  ☐ YES  DISEASE NAME: _____
                WHEN: _____
- ■ HAVE YOU EVER RECEIVED A BLOOD TRANSFUSION?  ☐ NO   ☐ YES
- ■ DO YOU HAVE ANY MEDICATION ALLERGIES?  ☐ NO · ☐ YES (           )
  DO YOU HAVE ANY FOOD ALLERGIES?        ☐ NO · ☐ YES (           )
  OTHER: _____
- ■ ARE YOU CURRENTLY TAKING ANY MEDICATION?
  ☐ NO  ☐ YES  (MEDICATION NAME: _____)

A3 {
- ■ DO YOU SMOKE CIGARETTES? ☐ YES   ☐ NO   ☐ I DID IN THE PAST
                (CIGARETTES PER DAY: ___, APPROX. _____ YEARS)
- ■ DO YOU DRINK ALCOHOL? ☐ NO   ☐ YES   ☐ I DID IN THE PAST
  (TYPE: ___, NUMBER OF DRINKS PER OCCASION: ___ ☐ DAILY ☐ SOMETIMES ☐ 2 TO 3 TIMES PER MONTH)

A4 {
- ■ MEDICAL HISTORY OF CLOSE RELATIVES
  DISEASE NAME: _____
  WHEN: _____

FIG. 6

MEDICAL QUESTIONNAIRE CREATION ASSIST DEVICE, METHOD, AND NON-TRANSITORY COMPUTER-READABLE STORAGE MEDIUM STORING PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2019/026069, filed Jul. 1, 2019, which application claims priority from Japanese Patent Application No. 2018-134034, filed Jul. 17, 2018, which applications are incorporated herein by reference in their entireties.

TECHNICAL FIELD

Embodiments of this invention relate to a medical questionnaire creation assist device having a function of assisting creation of a medical questionnaire of a patient, for example, and a medical questionnaire creation assist method and a non-transitory computer-readable storage medium storing a program executed by this device.

BACKGROUND ART

In medical institutions such as hospitals, doctor offices, and clinics, in the case of a first visit, it is common for a patient him or herself or a medical staff member such as a nurse to first fill out a medical questionnaire, and then a physician carries out a consultation on the basis of this medical questionnaire. However, because the medical questionnaire is created and stored on a per medical institution basis, when the patient visits a different medical institution, the patient must fill out the medical questionnaire once again even if symptoms are identical, which is a burdensome task for the patient. Further, even when the patient visits the same medical institution again shortly thereafter with the same symptoms after the treatment has ended, the patient may be required to fill out the medical questionnaire again, which is also a burden on the patient.

Therefore, in the related art, for example, a system, in which medical questionnaire data of a patient are stored in a clinical database together with basic patient data including attributes and the like, and the medical questionnaire data of the applicable patient can be read and used in a consultation as needed, is proposed (refer to Patent Document 1, for example). In this system, the medical questionnaire, once created, can be utilized not only at the same hospital but also at different hospitals or doctor offices within the region, for example, on the basis of approval of the patient, and a reduction in the burden on the patient or the medical staff can be expected.

CITATION LIST

Patent Literature

Patent Document 1: JP 2002-366655 A

SUMMARY OF INVENTION

Technical Problem

However, in the system described in Patent Document 1, while the created medical questionnaire can be reused, there is no change in the fact that the patient him or herself or the medical staff must fill out all items of the medical questionnaire at the first visit. Therefore, the burden on the patient or medical staff at the first visit is still not improved. In particular, when the patient is an elderly person or a child, or when the physical condition of the patient is worsening due to fever, pain, or the like, it may not be possible to fill out the medical interview contents without omission or to fill out the medical questionnaire properly, making it impossible to provide a highly effective medical questionnaire to the doctor.

This invention has been made with reference to the above circumstances, and is an attempt to provide a technology that makes it possible to more effectively create a medical questionnaire.

Solution to Problem

In order to solve the problems described above, a first aspect according to this invention is a medical questionnaire creation assist device including a clinical data acquisition unit configured to acquire clinical data of the past of a patient on the basis of personal identification information of the patient, a basic data creation unit configured to create medical questionnaire basic data of the patient on the basis of medical questionnaire template data including an input region related to a plurality of medical interview items that are predetermined and the clinical data being acquired, a medical questionnaire data creation unit configured to receive input data of statement information regarding a symptom of the patient and add the input data to the medical questionnaire basic data and create medical questionnaire data of the patient, and an output unit configured to output the medical questionnaire data being created.

According to the first aspect, when a patient or a medical staff fills out a medical questionnaire at a first visit, for example, the medical questionnaire creation assist device acquires the clinical data of the past of the patient and, on the basis of the clinical data being acquired and the medical questionnaire template data, creates medical questionnaire basic data pertaining to the parent. Then, when the patient or the medical staff inputs, in the medical questionnaire creation assist device, statement information related to an incomplete medical interview item in the medical questionnaire template data described above, such as the reason for the visit of this time, symptoms, for example, the statement information being input is added to the incomplete medical interview item of the medical questionnaire template data described above, and the medical questionnaire data are output after this addition.

Accordingly, when creating the medical questionnaire at a first outpatient visit, the patient or the medical staff need only input statement information related to the reason for the visit of this time, current symptoms, symptoms changes, and the like, eliminating the need to input statement information for all medical interview items. Therefore, the burden on the patient or the medical staff when creating the medical questionnaire is significantly reduced. Further, the medical questionnaire can be accurately created in a short time, making it possible to shorten the consultation wait time of the patient and improve the efficiency of outpatient care. This advantageous effect is highly effective in reducing the burden on, in particular, patients of such as the elderly or children and patients with a physical condition worsening due to fever, pain, or the like, and in maintaining the information of the medical questionnaire with high accuracy.

Further, because all or a portion of the creation process of the medical questionnaire is performed by the medical questionnaire creation assist device, the creation process is distributed and being, compared to when, for example, the entire creation process is collectively performed by a terminal of a healthcare provider or a server device of a hospital, it is possible to alleviate the concentration of a processing load on the terminal of the healthcare provider or the hospital server device.

According to a second aspect of this invention, in the first aspect described above, the device further includes a health management data acquisition unit configured to acquire health management data indicating a health state or a lifestyle state of the patient. The basic data creation unit is configured to create the medical questionnaire basic data of the patient on the basis of the medical questionnaire template data, the clinical data being acquired, and the health management data being acquired.

According to the second aspect, when the medical questionnaire basic data are created, for example, in addition to the clinical data acquired from an electronic medical records (EMR) server or an electronic health records (EHR) server provided so as to be shared by a plurality of medical institutions within the region, health management data acquired from a mobile information terminal possessed by the patient can be added. Therefore, the patient and the medical staff need not measure health management data such as height, weight, body temperature, and blood pressure, when creating the medical questionnaire, for example, making it possible to further reduce the load and time required to create the medical questionnaire data.

According to a third aspect of this invention, in the first or second aspect described above, the basic data creation unit is configured to apply, to the medical questionnaire basic data, first marking information highlighting a position of an incomplete medical interview item included in the medical questionnaire basic data being created, and cause the display device to display the medical questionnaire basic data with the first marking information being applied.

According to the third aspect, an incomplete medical interview item included in the medical questionnaire basic data is applied with the first marking information highlighting this incomplete medical interview item and displayed. Therefore, the patient or the medical staff can clearly recognize which medical interview item could not be filled by the clinical data of the past or the health management data, making it possible to create medical questionnaire data without omission.

According to a fourth aspect of this invention is, in the first or second aspect, the basic data creation unit is configured to add information indicating a generation date and time, such as a diagnosis date and time or a measurement date and time, to data entered in the medical questionnaire basic data, and cause the display device to display the medical questionnaire basic data with the information indicating the generation date and time being added.

According to the fourth aspect, information indicating the generation date and time is added to the data entered in the medical questionnaire basic data, and thus, when a medical staff such as a physician refers to the medical questionnaire data, it is possible to precisely determine the reliability of the data entered for each medical interview item and make a diagnosis.

According to a fifth aspect of this invention, in the fourth aspect, when the generation date and time of the data entered in the medical questionnaire basic data being created is earlier than a current time by a period set in advance or longer, the basic data creation unit is configured to apply second marking information indicating a degree of reliability to the data, and cause the display device to display the medical questionnaire basic data with the second marking information being applied.

According to the fifth aspect, the medical staff, such as a physician, for example, can identify the degree of reliability from the freshness of the data entered in the medical questionnaire basic data by the second marking information, making it possible to easily and reliably determine the reliability of the data entered for each medical interview item when referring to the medical questionnaire data.

According to a sixth aspect of this invention, in the first or second aspect described above, the medical questionnaire data creation unit is configured to cause the display device to display list information of input candidates for an incomplete medical interview item included in the medical questionnaire basic data.

According to the sixth aspect, the patient or the medical staff can input a symptom, for example, by simply selecting an applicable symptom from the list information of input candidates by a touch operation, making it possible to further reduce the time and effort required to create the medical questionnaire.

According to a seventh aspect of this invention, in the first to sixth aspects described above, the output unit is configured to transmit, in response to a medical questionnaire data creation end operation, the medical questionnaire data being created to an external terminal set in advance.

According to the seventh aspect, for example, when the medical questionnaire data creation operation has ended, the medical questionnaire data are automatically transmitted to the terminal of the physician, for example. Therefore, the physician can study the contents of the medical questionnaire data immediately after creation of the medical questionnaire data has ended, making it possible to further shorten the consultation wait time of the patient.

According to an eighth aspect of this invention, in the first to seventh aspects described above, the device further includes a disclosure range setting unit configured to set, for each of the plurality of medical interview items of the medical questionnaire data being created, information restricting a disclosure range of the statement information for the medical interview item.

According to the eighth aspect, for example, in a state in which the medical questionnaire data are stored as a portion of the clinical data in the EMR server or the EHR server, when a view request for the medical questionnaire data occurs from a person who wants to view the information other than the patient him or herself, it is possible to restrict the disclosure range of the medical questionnaire data in accordance with a strength of a relationship of the person, who wants to view, with the patient, for example.

According to a ninth aspect of this invention, a medical questionnaire creation assist device includes a statement information acquisition unit configured to acquire input data of statement information regarding a symptom of a patient, a basic data creation unit configured to create medical questionnaire basic data of the patient on the basis of medical questionnaire template data including an input region related to a plurality of medical interview items that are predetermined and the input data being acquired, a data acquisition unit configured to acquire, on the basis of personal identification information of the patient, at least one of clinical data of the past of the patient and health management data indicating a health state or a lifestyle state of the patient, a medical questionnaire data creation unit configured to select, from at least one of the clinical data and the health management data being acquired, data related to the statement information, and add the data being selected to the medical questionnaire basic data, and create medical questionnaire data of the patient, and an output unit configured to output the medical questionnaire data being created.

According to the ninth aspect, data related to the current contents of the statement data of the patient are selected from at least one of the clinical data of the past of the patient included in the EMR or EHR data and the health management data and lifestyle data of the patient included in the PHR data, and are automatically entered in the medical questionnaire data. This makes it possible to create medical questionnaire data in which, from among the clinic information of the past as well as the health information and lifestyle information, sufficient necessary information has been entered in accordance with the statement contents of the condition of the patient.

Advantageous Effects of Invention

That is, according to each aspect of this invention, it is possible to provide a technology that makes it possible to more effectively create or manage a medical questionnaire.

BRIEF DESCRIPTION OF DRAWINGS

FIG. 6 is a drawing illustrating an example of a medical questionnaire.

DESCRIPTION OF EMBODIMENTS

Now, with reference to the drawings, an embodiment of the present invention is described.

Application Example

First, an application example of a medical questionnaire creation assist device according to an embodiment of this invention will be described.

Figure 1:
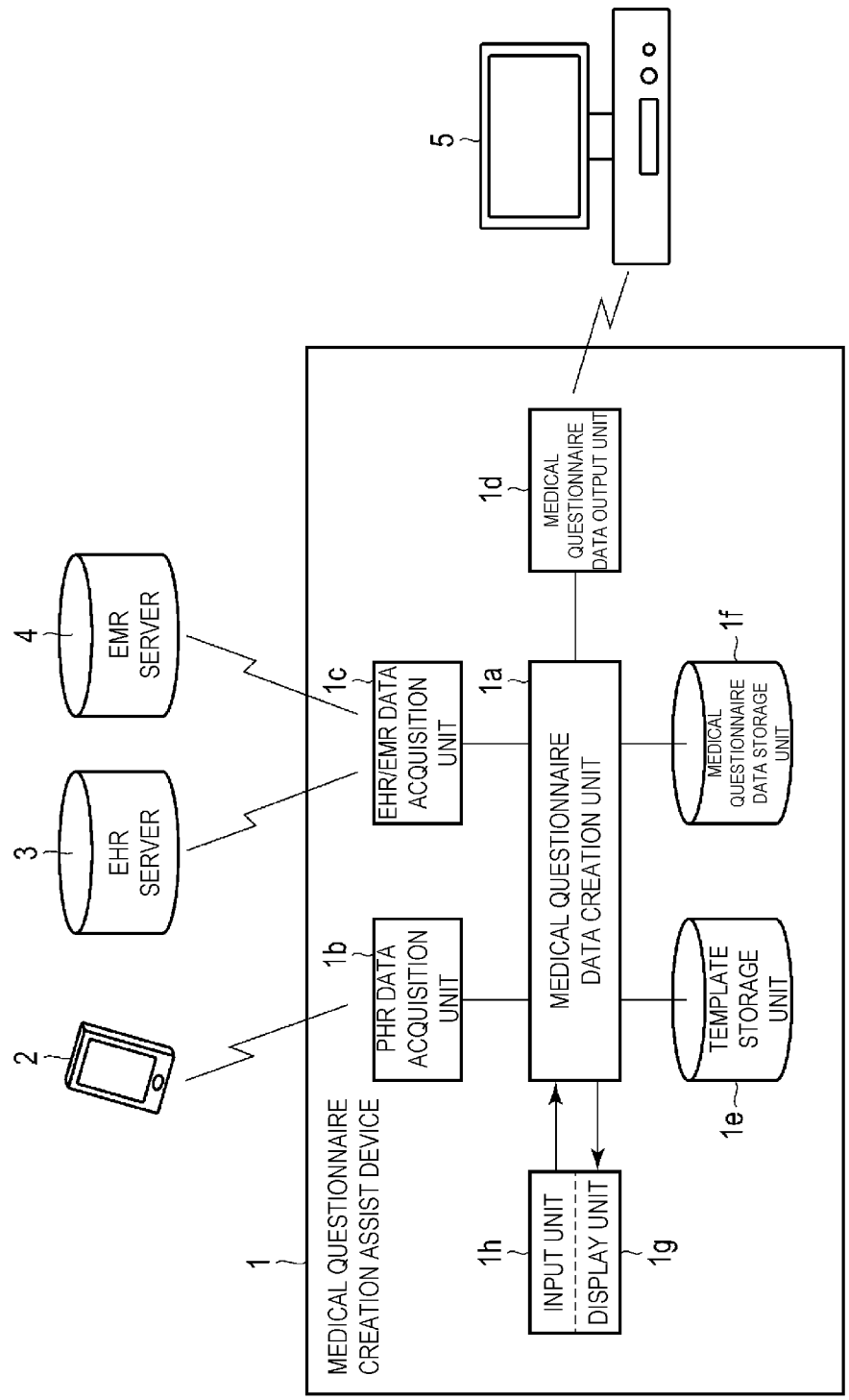
FIG. 1 is a block diagram illustrating an application example of a medical questionnaire creation assist device according to an embodiment of this invention.

FIG. 1 is a block diagram illustrating an application example of the medical questionnaire creation assist device according to the embodiment of this invention along with peripheral devices.

A medical questionnaire creation assist device 1 is used in, for example, a medical institution such as a hospital, a doctor office, or a clinic, by a patient him or herself or a medical staff member such as a nurse to create a medical questionnaire of the patient, and is constituted by, for example, a tablet terminal.

Note that the medical questionnaire creation assist device 1 is not limited to a tablet terminal, and may be a personal computer or a portable personal computer installed in a waiting room of a medical institution or the like, or may be provided as one of the enhanced functions on a mobile information terminal such as a smart phone possessed by the patient, an electronic medical records (EMR) server provided for each medical institution, or an electronic health records (EHR) server provided so as to be shared by a plurality of medical institutions within a region.

The medical questionnaire creation assist device 1 includes, as storage function units, a program storage unit as well as a template storage unit 1e and a medical questionnaire data storage unit 1f. Of these, the template storage unit 1e stores the medical questionnaire template data. Medical interview items differ for each clinical department, and thus a plurality of types of medical questionnaire template data are prepared. The medical questionnaire data storage unit 1f is used to save electronic data of the medical questionnaire created by a medical questionnaire data creation unit 1a.

Further, the medical questionnaire creation assist device 1 includes, as input/output function units, a display unit 1g and an input unit 1h. The display unit 1g and the input unit 1h are constituted by a touch panel type device in which an input detection sheet of a pressure sensitive type or an electrostatic type is disposed on a display screen of a liquid crystal display device or an organic electroluminescent (EL) display device, for example.

Furthermore, the medical questionnaire creation assist device 1 includes, as control function units, the medical questionnaire data creation unit 1a, a personal health records (PHR) data acquisition unit 1b configured to acquire PHR data, an EHR/EMR data acquisition unit 1c configured to acquire EHR data or EMR data, and a medical questionnaire data output unit 1d. These control function units are all realized by causing a hardware processor to execute a program stored in the program storage unit (not illustrated).

The PHR data acquisition unit 1b acquires the PHR data of the patient from a mobile information terminal 2 such as a smart phone possessed by the patient. The PHR data include health data indicating a health state of the user and lifestyle data indicating a lifestyle state of the user. The health data include biometric data such as, for example, height, weight, blood pressure value, heart rate, blood glucose level, and body temperature. The lifestyle data include, for example, activity amount, hours of sleep, food intake menu, and number of steps. These are also collectively referred to as health management data.

The EHR/EMR data acquisition unit 1c acquires the EHR data or the EMR data of the patient from an EHR server 3 or an EMR server 4. The EHR data or the EMR data include patient basic data and clinical data. The patient basic data include, for example, name, gender, date of birth, address, contact information, and occupation. The clinical data include, for example, medical examination data and information on an electronic chart created by a physician. The information on the electronic chart includes, for example, disease names and symptoms, treatment progress, presence or absence of surgical experience, test data, and medication information as well as history of transfusions, presence or absence of medicine or food allergies, cigarettes and alcohol intake status, and information indicating the medical history of close relatives.

The medical questionnaire data creation unit 1a has, for example, the following process functions.

(1) A process of receiving an input of personal identification information PID, such as the name and the date of birth of the patient, and determining whether clinical records of the patient are stored on the EMR server 4 of the medical institution or the EHR server 3 in the region on the basis of the personal identification information PID. Note that, when the patient has a consultation card that was used during a past visit, the medical questionnaire data creation unit 1a may read the personal identification information PID from the consultation card and determine the presence or absence of a clinical record on the basis of this personal identification information PID. The consultation card also includes a consultation card issued by another medical institution in the region other than that of its own medical institution.

(2) A process of acquiring the EMR data or the EHR data of the patient from the EMR server 4 or the EHR server 3 by the EHR/EMR data acquisition unit 1c when, as a result of the determination described above, a clinical record of the patient exists.

(3) A process of acquiring the most recent PHR data from the mobile information terminal 2 of the patient by the PHR data acquisition unit 1b.

(4) A process of editing medical questionnaire basic data using the medical questionnaire template data stored in the template storage unit 1e, the acquired EHR data or EMR data described above, and the PHR data, and displaying medical questionnaire basic data on the display unit 1g.

(5) A process of receiving statement information input in the input unit 1h by the patient or the medical staff regarding incomplete medical interview items in the medical questionnaire basic data being displayed, adding the statement information to the medical questionnaire basic data described above to complete the medical questionnaire data, and displaying on the display unit 1g and also saving in the medical questionnaire data storage unit 1f the medical questionnaire data being completed.

The medical questionnaire data output unit 1d reads the medical questionnaire data being created from the medical questionnaire data storage unit 1f described above, and transmits the medical questionnaire data to a physician terminal 5.

With a configuration such as described above, when the patient or the medical staff fills out the medical questionnaire at a first visit, in the medical questionnaire creation assist device 1 constituted by a tablet terminal, for example, when the patient name and date of birth are input, or when the personal identification information PID of the consultation card used in the past visit is read, the medical questionnaire creation assist device 1 determines whether or not a clinical record of the patient is registered in the EHR/EMR data. When a clinical record is registered, the EMR data or the EHR data of the applicable patient are acquired from the EMR server 4 or the EHR server 3, and the PHR data are further acquired from the mobile information terminal 2. Then, on the basis of each of this acquired data and the medical questionnaire template data, medical questionnaire basic data pertaining to the patient are created.

Further, when the patient or the medical staff such as a nurse inputs, in the medical questionnaire creation assist device 1, statement information related to incomplete medical interview items, such as the reason for the visit of this time, symptoms, for example, of the medical questionnaire template data described above, the statement information being input is added to the incomplete medical interview items of the medical questionnaire template data described above, and the medical questionnaire data after this addition are stored in the medical questionnaire data storage unit 1f and also transmitted to the physician terminal 5.

Accordingly, when creating the medical questionnaire at a first outpatient visit, the patient or medical staff such as a nurse need only input statement information related to the reason for the visit of this time, current symptoms, symptoms changes, and the like, eliminating the need to input statement information for all medical interview items. Therefore, the burden on the patient or the medical staff when creating the medical questionnaire is significantly reduced.

Further, the medical questionnaire can be accurately created in a short time, making it possible to shorten the consultation wait time of the patient and improve the efficiency of outpatient care. This advantageous effect is highly effective in reducing the burden on, in particular, patients of such as the elderly or children and patients with a physical condition worsening due to fever, pain, or the like, and in maintaining the information of the medical questionnaire with high accuracy.

First Embodiment

CONFIGURATION EXAMPLE (1) System

Figure 2:
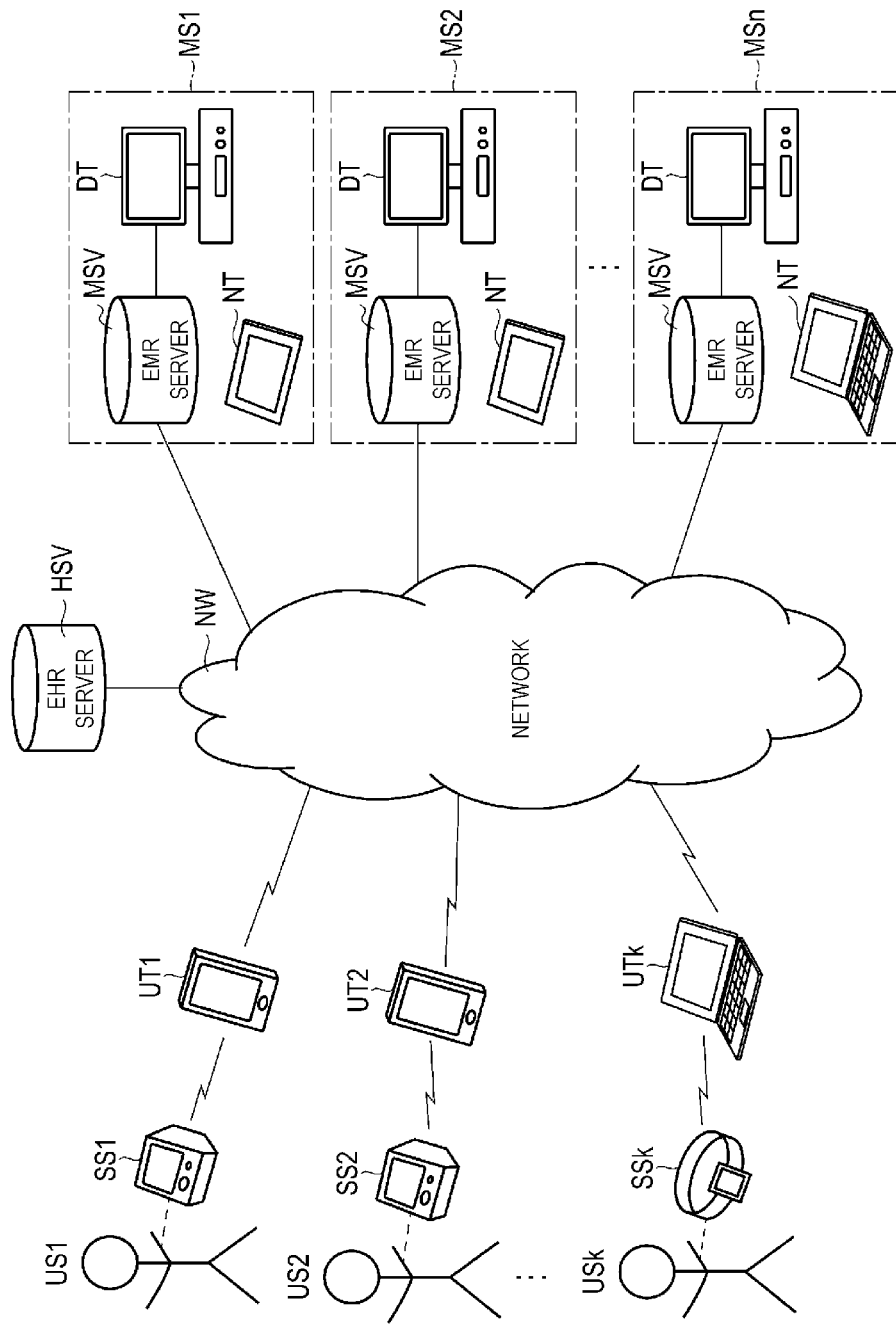
FIG. 2 is a drawing illustrating an example of a regional medical system that includes the medical questionnaire creation assist device according to the embodiment of this invention.

FIG. 2 is a drawing illustrating an overall configuration of a medical information management system including a medical questionnaire creation assist device according to the embodiment, with MS1, MS2, . . . , MSn denoting medical institutions such as hospitals, doctor offices, clinics, and the like.

Each of the medical institutions MS1, MS2, . . . , MSn includes an EMR server MSV, a medical questionnaire creation assist terminal NT having the functions of the medical questionnaire creation assist device, and a physician terminal DT. The EMR server MSV, the medical questionnaire creation assist terminal NT, and the physician terminal DT are capable of data transmission between one another via, for example, a hospital local area network (LAN) or a hospital wireless LAN, and are further connectible to a network NW, which is external, via the hospital LAN or the hospital wireless LAN described above.

The EMR server MSV stores and manages, for each medical institution MS1, MS2, . . . , MSn, the clinical data of patients who visited the medical institutions MS1, MS2, . . . , MSn, in association with the patient basic data. The patient basic data include attribute information such as, for example, name, gender, age, address, contact information, and occupation. The medical data are mainly composed of information of an electronic chart created by a physician, and includes, for example, disease names and symptoms, treatment progress, presence or absence of surgeries, test data, and medication information as well as presence or absence of allergies to medicines or foods, cigarettes and alcohol intake status, and medical history information of close relatives.

Further, the EMR server MSV described above is capable of data transmission with an EHR server HSV via the network NW. The network NW includes, for example, a public network, such as the Internet, and an access network for accessing this public network. As the access network, for example, the hospital LAN or wireless LAN described above is used, but a wired telephone network, a community antenna television (CATV) network, a mobile phone network, a public wireless LAN, or the like can also be used.

The EHR server HSV is disposed by region, for example, by city, ward, town, or village. Then, the EHR server HSV stores and manages the basic data and the clinical data of the patient uploaded from the EMR server MSV of the medical institutions MS1 to MSn in the region as the EHR data. Thus, the EHR server HSV enables the sharing of clinical data of the patients between each of the medical institutions MS1 to MSn in the region.

Mobile information terminals UT1 to UTk are constituted by, for example, smart phones, tablet terminals, and portable personal computers, and each have a function of respectively acquiring measurement data acquired by sensing devices SS1 to SSk via a near-range wireless network and storing the measurement data as the PHR data.

As the sensing devices SS1 to SSk, a blood pressure monitor, an electrocardiograph, a thermometer, an activity meter, a weight scale, a body composition meter, and a biological information measuring device such as a wearable terminal or a health meter equipped with the measurement functions of these measurement instruments in a multifaceted manner are used, for example. As the near-range wireless network, a wireless network adopting a low-power wireless data communication standard such as Bluetooth (trade name) is used, for example, but is not limited thereto.

Further, the mobile information terminals UT1 to UTk have a function of transmitting the stored PHR data described above to the medical questionnaire creation assist terminal NT when a request for transmission of PHR data is received from the medical questionnaire creation assist terminal NT in a communication area of the hospital wireless LAN of the medical institutions MS1 to MSn.

Figure 3:
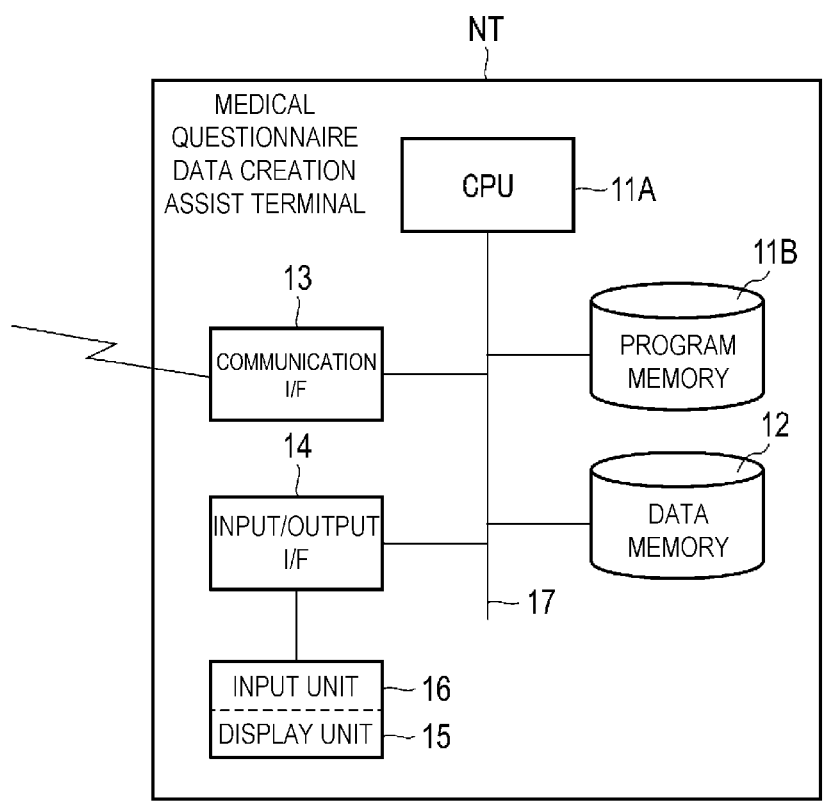
FIG. 3 is a block diagram illustrating an example of a hardware configuration of the medical questionnaire creation assist device according to the embodiment of this invention.

(2) Medical Questionnaire Creation Assist Terminal NT
(2-1) Hardware Configuration FIG. 3 is a block diagram illustrating an example of a hardware configuration of the medical questionnaire creation assist terminal NT.

The medical questionnaire creation assist terminal NT includes a hardware processor 11A such as a central processing unit (CPU), for example. Then, a program memory 11B, a data memory 12, a communication interface (communication I/F) 13, and an input/output interface (input/output I/F) 14 are connected to this hardware processor 11A via a bus 17.

The communication I/F 13 performs data transmission between the EMR server MSV and the physician terminal DT via, for example, the hospital wireless LAN, and also performs data transmission with the EHR server HSV via the hospital wireless LAN described above and the external network NW. Note that instead of using the hospital wireless LAN, the communication I/F 13 can use a mobile phone network or a public wireless LAN to carry out data transmission with the EHR server HSV via the network NW.

A display unit 15 and an input unit 16 are connected to the input/output I/F 14. The display unit 15 and the input unit 16 are constituted by a touch panel type input/output device in which an input detection sheet of a pressure sensitive type or electrostatic type is disposed on a display screen of a liquid crystal display device or an organic EL display device, for example. The input/output I/F 14 causes the display unit 15 to display the basic data and the completed data of the medical questionnaire generated by the CPU 11A, and also transmits statement information, such as symptoms, manually input in the input unit 16 to the CPU 11A.

The program memory 11B is a combination of a non-volatile memory such as a hard disk drive (HDD) and a solid state drive (SSD) capable of reading and writing at any time, and a non-volatile memory such as a read-only memory (ROM) as storage media, for example, and stores programs required to execute various control processes related to the embodiment.

The data memory 12 is a combination of a non-volatile memory such as an HDD or an SSD capable of reading and writing at any time, and a volatile memory such as a random-access memory (RAM) as storage media, for example. Then, the data memory 12 is used to store the data and the template data acquired and created in the course of executing various processes related to the creation of the medical questionnaire.

(2-2) Software Configuration

Figure 4:
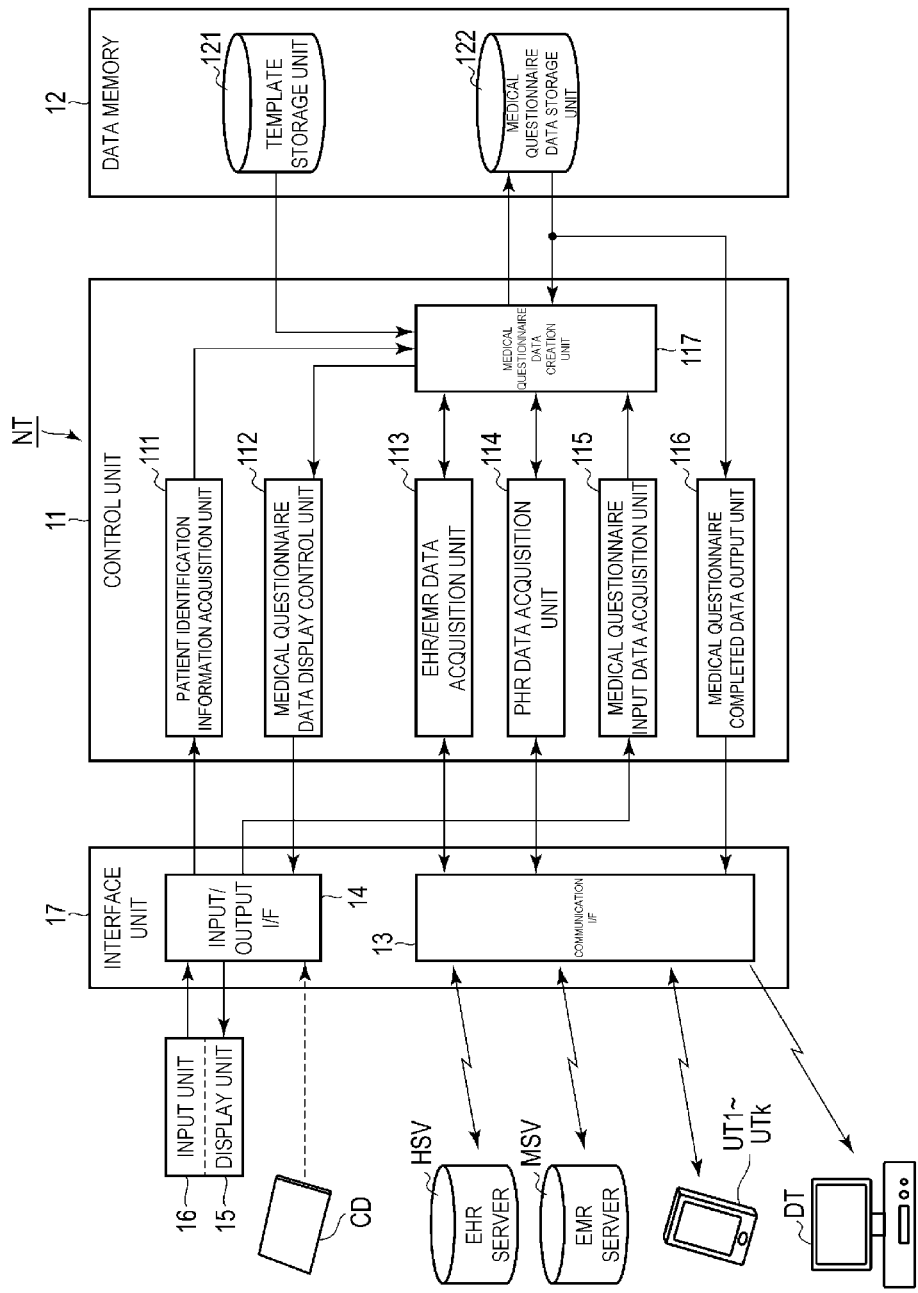
FIG. 4 is a block diagram illustrating an example of a software configuration of the medical questionnaire creation assist device according to the embodiment of this invention.

FIG. 4 is a block diagram illustrating a software configuration of the medical questionnaire creation assist terminal NT according to the embodiment of this invention, in association with the hardware configuration illustrated in FIG. 3.

A storage region of the data memory 12 is provided with a template storage unit 121 and a medical questionnaire data storage unit 122. The template storage unit 121 stores the template data required to create the medical questionnaire in advance. The medical interview items of the medical questionnaire differ for each clinical department. Therefore, the medical questionnaire template data described above are created for each clinical department and stored in the template storage unit 121. The medical questionnaire data storage unit 122 is used to store the basic data and the completed data of the medical questionnaire created by a medical questionnaire data creation unit 117.

A control unit 11 is constituted by the hardware processor 11A described above and the program memory 11B described above and, as processing function units by the software, includes a patient identification information acquisition unit 111, a medical questionnaire data display control unit 112, an EHR/EMR data acquisition unit 113, a PHR data acquisition unit 114, a medical questionnaire input data acquisition unit 115, a medical questionnaire completed data output unit 116, and the medical questionnaire data creation unit 117. These processing function units are all realized by causing the hardware processor 11A described above to execute a program stored in the program memory 11B.

The patient identification information acquisition unit 111 acquires, via an input/output I/F 14, the personal identification information PID of the patient input by the patient in the input unit 16 or the personal identification information PID of the patient read from a consultation card CD. Then, the process of notifying the medical questionnaire data creation unit 117 of the acquired personal identification information PID is performed. The personal identification information PID of the patient described above may include, for example, "name" and "date of birth", but may also be a public personal identification number such as a "consultation card registration number" of a consultation card issued by a medical institution in the region, a driver's license, a passport, or a My-Number (Individual Number) card.

The medical questionnaire data display control unit 112 performs a process of causing the display unit 15 to display the basic data and completed data of the medical questionnaire (hereinafter, also simply referred to as medical questionnaire data) IVS created by the medical questionnaire data creation unit 117 via the input/output I/F 14.

The EHR/EMR data acquisition unit 113, in accordance with an instruction of the medical questionnaire data creation unit 117, transmits an acquisition request RQ for the EHR data or the EMR data of the patient from the communication I/F 13 to the EHR server HSV or the EMR server MSV. Then, in response to the acquisition request RQ described above, the EHR data or EMR data DT1 transmitted from the EHR server HSV or the EMR server MSV are received via the communication I/F 13, and delivered to the medical questionnaire data creation unit 117.

The PHR data acquisition unit 114, in accordance with an instruction of the medical questionnaire data creation unit 117, transmits the acquisition request for the PHR data of the patient from the communication I/F 13 to the mobile information terminal UTi of the patient via the hospital wireless LAN. Then, in response to the acquisition request described above, a process of receiving, via the communication I/F 13, PHR data DT2 transmitted from the mobile information terminal UTi, and passing the PHR data DT2 to the medical questionnaire data creation unit 117 is performed.

The medical questionnaire input data acquisition unit 115 performs a process of importing, via the input/output I/F 14, the statement information of a medical interview manually input by the patient or the medical staff in the input unit 16, and passing the statement information to the medical questionnaire data creation unit 117.

The medical questionnaire completed data output unit 116 performs a process of reading the completed data of the medical questionnaire created by the medical questionnaire data creation unit 117 from the medical questionnaire data storage unit 122, and transmitting the completed data of the medical questionnaire from the communication I/F 13 to the physician terminal DT.

The medical questionnaire data creation unit 117 is equipped with the following processing functions.

(1) A process of querying, from the EHR/EMR data acquisition unit 113, when the patient identification information PID of a first-visit patient is received from the patient identification information acquisition unit 111, whether or not the applicable patient is registered in the EMR server MSV or the EHR server HSV on the basis of the personal identification information PID, and determining whether or not the patient is registered on the basis of the answer result.

(2) A process of transmitting, when it is determined that the patient is registered in either the EMR server MSV or the EHR server HSV, the acquisition request RQ for the EMR data or the EHR data from the EHR/EMR data acquisition unit 113 to the EMR server MSV or the EHR server HSV described above, and acquiring the EMR data or the EHR data DT1 of the applicable patient.

(3) A process of transmitting, on the basis of the entered personal identification information PID of the patient described above, the acquisition request for the PHR data from the PHR data acquisition unit 114 to the mobile information terminal UTi possessed by the patient, and acquiring the PHR data DT2 of the applicable patient.

(4) Selecting, on the basis of the medical questionnaire template data described above, information corresponding to the medical interview items from the acquired EMR data or EHR data DT1 and the PHR data DT2 described above, and editing the basic data of the medical questionnaire on the basis of the selected information and the medical questionnaire template data described above. Then, a process of causing the display unit 15 to display the edited medical questionnaire basic data by the medical questionnaire data display control unit 112.

(5) Acquiring, when the patient or the medical staff inputs statement information DL1 in the input unit 16 for incomplete medical interview items included in the medical questionnaire basic data being displayed, the statement information DL1 via the medical questionnaire input data acquisition unit 115, and adding the statement information to the medical questionnaire basic data described above and creating the completed data IVS of the medical questionnaire. Then, a process of causing the completed data IVS of the medical questionnaire being created to be displayed on the display unit 15 by the medical questionnaire data display control unit 112 and also stored in the medical questionnaire data storage unit 122.

Note that, among the processing functions described above, (1) to (4) constitute a creation function unit for the medical questionnaire basic data, and (5) constitutes a creation function unit for the medical questionnaire data.

Operation Example

Next, a medical questionnaire creation assist processing operation by the medical questionnaire creation assist terminal NT configured as described above will be described.

Figure 5:
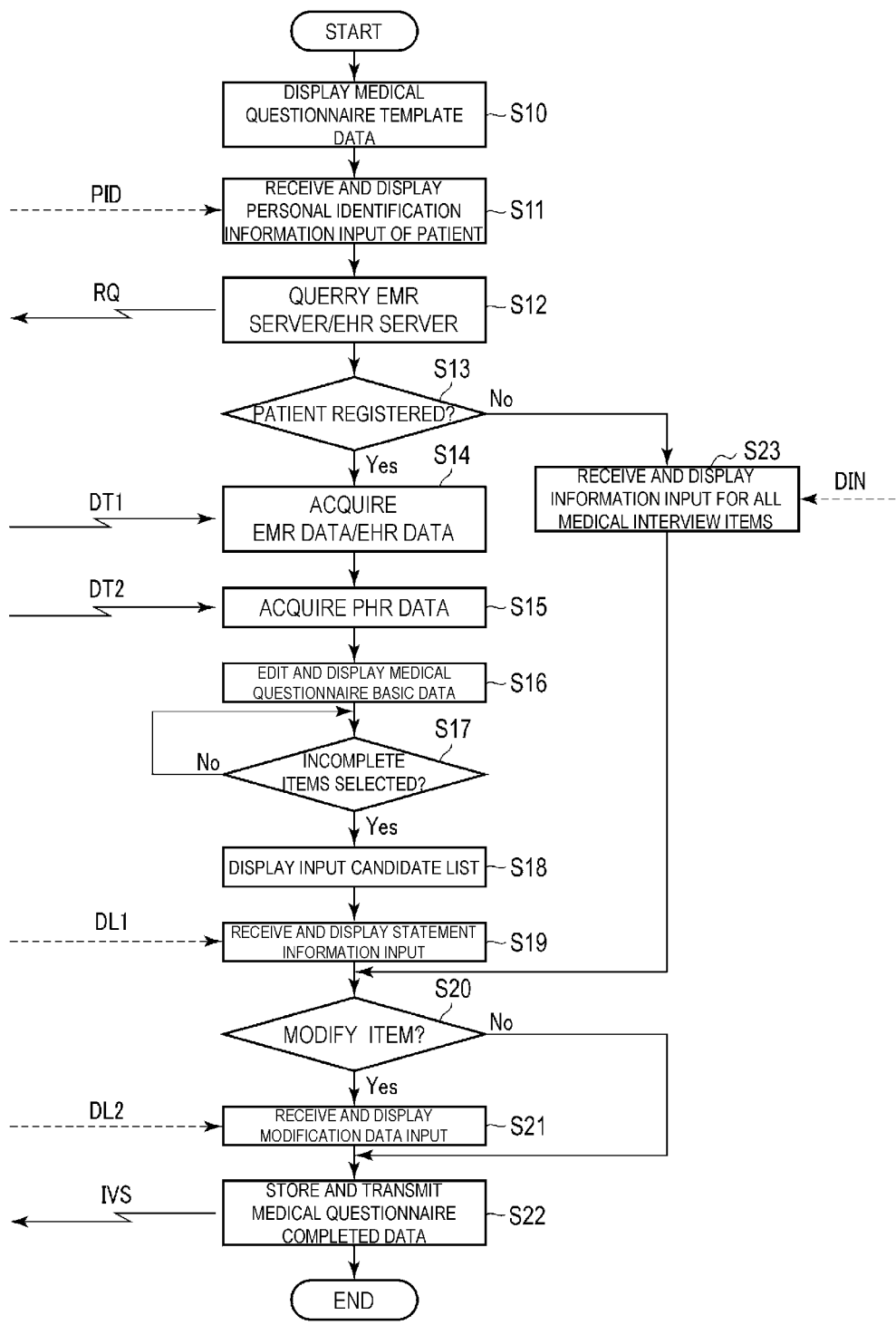
FIG. 5 is a flowchart illustrating an example of a medical questionnaire creation assist process executed by the medical questionnaire creation assist device illustrated in FIG. 4.

FIG. 5 is a flowchart illustrating a processing procedure and processing contents of the medical questionnaire creation assist terminal NT.

(1) Identification of Patient

In a clinical outpatient department, when the patient or the medical staff such as a nurse, activates the medical questionnaire assist terminal NT, under the control of the medical questionnaire data creation unit 117, first, in step S10, the medical questionnaire template data corresponding to the clinical department are read from the template storage unit 121 and, by the control of the medical questionnaire data display control unit 112, displayed on the display unit 15.

In this state, that the patient him or herself or the medical staff inputs the personal identification information PID of the patient in the input unit 16 or causes a card reader of the input unit 16 to read the consultation card previously created by the medical institution or another medical institution in the region. Note that, for example, the name and the date of birth of the patient are used as the personal identification information PID of the patient.

Then, in step S11, under the control of the medical questionnaire data creation unit 117, the personal identification information PID being input or the consultation card registration number being read from the consultation card as described above is imported and, in step S12, under the control of the medical questionnaire data creation unit 117, the personal identification information PID or the consultation card registration number described above is used as a key to query the EMR server MSV or the EHR server HSV regarding the presence or absence of registration of the patient.

In the EMR server MSV or the EHR server HSV, a process of searching a database of the patient basic data in response to the query described above is performed, and the search result is returned to the medical questionnaire creation assist terminal NT serving as the source of the query. Upon receiving the search result described above, in step S13, the medical questionnaire creation assist terminal NT, under the control of the medical questionnaire data creation unit 117, first determines whether the patient is registered.

(2) Acquisition of EHR/EMR Data

As a result of the determination described above, when the patient is registered, in step S14, the medical questionnaire data creation unit 117 instructs the EHR/EMR data acquisition unit 113 to acquire the EHR data or the EMR data. As a result, the EHR/EMR data acquisition unit 113 transmits the data acquisition request RQ to the EMR server MSV or the EHR server HSV, and acquires the EMR data or the EHR data DT1 of the applicable patient. The EMR data or the EHR data DT1 are temporarily saved in a work storage region in the data memory 12.

By the acquisition process described above, when the patient has a past history of visiting another clinical department of the medical institution, the EMR data DT1 of the patient is acquired from the EMR server of the medical institution. On the other hand, even when there is no visit history of the medical institution, when there is a history of visiting another medical institution in the region, the EHR data DT1 of the patient are acquired from the EHR server HSV.

(3) Acquisition of PHR Data

Next, the medical questionnaire data creation unit 117, in step S15, instructs the PHR data acquisition unit 114 to acquire the PHR data. As a result, the PHR data acquisition unit 114 transmits an acquisition request for the PHR data to the mobile information terminal UTi of the patient, and acquires the PHR data DT2 of the applicable patient. The PHR data DT2 are also temporarily saved in the work storage region in the data memory 12.

(4) Creation of Medical Questionnaire Basic Data

Next, in step S16, the medical questionnaire data creation unit 117 performs edit processing on the medical questionnaire basic data as follows. That is, first, information corresponding to the medical interview items is selected from the EMR data or the EHR data DT1 and PHR data DT2 being acquired as described above, on the basis of the medical questionnaire template data. Then, the medical questionnaire data creation unit 117 edits the basic data of the medical questionnaire on the basis of the selected information and the medical questionnaire template data described above.

For example, as illustrated in FIG. 6, as medical interview items of the medical questionnaire template data, a patient personal identification information entry field A1, a biological information entry field B1, an entry field C for purpose of visit, symptoms, and the like, an entry field A2 for the medical history of the patient and the like, an entry field A3 for cigarettes and alcohol intake status, and an entry field A4 for the medical history of close relatives are prepared.

In this case, for example, first, information corresponding to the "name", "gender", "age", and "consultation card registration number" is selected from the patient basic data included in the EMR data or the EHR data DT1 and entered into the patient personal identification information entry field A1.

Next, for the entry fields A2, A3 and A4 of the medical questionnaire template data for the medical history and the like of the patient, information corresponding to "medical history", "presence or absence of a surgical experience", "history of transfusions", "presence or absence of medicine or food allergies", "prescribed medications", "cigarettes and alcohol intake status", and "medical history of close relatives" are respectively selected from clinical data (clinical records) included in the EMR data or the EHR data DT1, and entered into the corresponding fields.

Furthermore, information corresponding to "blood pressure", "height", "weight", and "today's body temperature" are respectively selected from the PHR data DT2 and entered into the biological information entry field B1 of the medical questionnaire template data.

Note that, when the EMR data or the EHR data DT1 and the PHR data DT2 described above are entered into the medical interview items of the medical questionnaire template, the medical questionnaire data creation unit 117 enters the date and time of creation or the date and time of measurement of the data. Further, at this time, in a case in which the date and time of creation or the date and time of measurement of the data are older than a preset period (for example, three years) from the current time, preferably the applicable data are marked with a warning mark indicating a degree of reliability. Then, when a physician refers to the medical questionnaire, for example, the physician can easily determine the reliability from the freshness of the data entered for each medical interview item.

The medical questionnaire data creation unit 117 passes the basic data of the medical questionnaire edited and created as described above to the medical questionnaire data display control unit 112. As a result, the basic data of the medical questionnaire described above are displayed on the display unit 15 via the input/output I/F 14 by the medical questionnaire data display control unit 112.

Note that, at this time, preferably a marking is applied to, among each of the medical interview items of the medical questionnaire basic data described above, medical interview items for which information is incomplete, in order to highlight the position of the incomplete medical interview items. Incomplete items include the entry field C for the purpose of the today's visit, symptoms, and the like as well as the fields among the entry fields A2, A3, A4 for medical history and the like and the entry field B1 for biological information in which information could not be entered by the EMR/EHR data and the PHR data. Examples of techniques for marking include a technique in which the entry field of the incomplete item is colored or surrounded by a thick frame. By applying a marking to the incomplete item, the patient or the medical staff can clearly recognize which medical interview items are incomplete.

(5) Manual Input of Medical Interview Statement Information

The patient or the medical staff ascertains an incomplete medical interview item on the basis of the displayed medical questionnaire basic data described above, and selects the incomplete item by a touch operation, for example, to input statement information for the incomplete item.

The medical questionnaire data creation unit 117, in step S17, detects the selection of the incomplete item described above and, in step S18, reads list information of input candidates from an input candidate storage region in the data memory 12, for example, and causes the display unit 15 to display the list information of input candidates by the medical questionnaire data display control unit 112.

For example, when the entry field C for the purpose of the today's visit, symptoms, and the like is selected as the incomplete item, the list information of a plurality of symptoms as candidates is read and displayed. Note that the list information of the input candidates described above may be a list of representative symptoms set in advance, but may be a list of symptoms corresponding to a disease that are prevalent in each season, or a list of symptoms corresponding to diseases to which the patient is susceptible to develop based on the medical history of the patient, for example.

Assume that, with the list information of the input candidates described above displayed, the patient or the medical staff selects the applicable symptom by a touch operation, or manually inputs, in the input unit 16, a description of a symptom not available among the input candidates. Then, the information indicating the symptom being input is acquired by the medical questionnaire input data acquisition unit 115 and passed to the medical questionnaire data creation unit 117. In step S19, the medical questionnaire data creation unit 117 adds the information indicating the symptom being input to the medical questionnaire basic data described above, and causes the medical questionnaire basic data after this addition to be displayed on the display unit 15 by the medical questionnaire data display control unit 112.

As such, the patient or the medical staff can input the purpose of the today's visit and the symptoms by a manual operation.

Further, assume that the patient or the medical staff selects, by a touch operation, a medical interview item corresponding to information, among the information entered in the entry fields A2, A3, A4 for medical history and the like and the entry field B1 for biological information, that has diverged from the current condition of the patient or is preferably not to be entered. The medical interview item being selected by this touch operation is detected in step S20. Then, when the patient or the medical staff inputs modification information DL2 in the input unit 16, the medical questionnaire data creation unit 117, in step S21, receives the modification data DL2 described above, modifies the information entered for the corresponding item, and causes the display unit 15 to display the modification result.

The input reception process of the statement information for an incomplete item and the input reception process of the modification information for an item to be modified described above are repeated until the patient or the medical staff performs an input end operation.

(6) Transmission of Medical Questionnaire Completed Data

In step S22, when the input end operation described above is detected, under the control of the medical questionnaire data creation unit 117, the medical questionnaire creation assist terminal NT causes the medical questionnaire data storage unit 122 to store the completed data of the medical questionnaire for which creation has ended. Along with this, in step S22, the medical questionnaire creation assist terminal NT, under the control of the medical questionnaire completed data output unit 116, reads the completed data IVS of the stored medical questionnaire described above from the medical questionnaire data storage unit 122, and transmits the medical questionnaire completed data IVS to the physician terminal DT via the communication I/F 13. Note that the medical questionnaire completed data IVS may be transmitted directly to the EMR server MSV.

Further, the medical questionnaire completed data IVS may be transmitted to a terminal, other than the physician terminal DT, such as the terminal of the patient him or herself or the terminal of the family. In this case, when the medical questionnaire completed data IVS are transmitted, preferably a confirmation step of the transmission destination is added and the medical questionnaire completed data IVS are transmitted only when the patient him or herself inputs authorization of the transmission destination name or address thereof. In this way, it is possible to prevent an inconvenience in which the medical questionnaire completed data IVS are transmitted without permission to a third party without the awareness or authorization of the patient him or herself.

(7) When Patient is not Registered in EMR Server or EHR Server

In step S23, when the patient is not registered in neither the EMR server MSV or the EHR server HSV in step S13 described above, the medical questionnaire creation assist terminal NT, under the control of the medical questionnaire input data acquisition unit 115 and the medical questionnaire data creation unit 117, executes a process of sequentially entering information DIN input by the patient or the medical staff in the input unit 16 into all medical interview items of the medical questionnaire template data.

(Actions and Effects)

As described above, in the embodiment, the medical questionnaire creation assist device NT, when creating a medical questionnaire for a patient, acquires the clinical data of past of the patient from the EMR server MSV or the EHR server HSV on the basis of the medical questionnaire template data, and also acquires the PHR data from the mobile information terminal UTi of the patient to create the basic data of the medical questionnaire. Then, the medical questionnaire creation assist device NT creates medical questionnaire completed data by adding medical interview statement information manually input by the patient or the medical staff to incomplete items in the medical questionnaire basic data, and notifies the physician terminal DT of the medical questionnaire completed data.

Accordingly, when creating the medical questionnaire at first visit, the patient or the medical staff such as a nurse need only manually input statement information related to the reason for the visit of this time, current symptoms, symptoms changes, and the like, eliminating the need to input statement information for all medical interview items. Therefore, the burden on the patient or the medical staff when creating the medical questionnaire is significantly reduced.

Further, the medical questionnaire can be accurately created in a short time, making it possible to shorten the consultation wait time of the patient and improve the efficiency of outpatient care. This advantageous effect is highly effective in reducing the burden on, in particular, patients of such as the elderly or children and patients with a physical condition worsening due to fever, pain, or the like, and in maintaining the information of the medical questionnaire with high accuracy.

Further, in the embodiment, when the medical questionnaire basic data are created, a marking is applied to, among each of the medical interview items, the medical interview items for which information is incomplete. Therefore, the patient or the medical staff can clearly recognize, without omission, which medical interview items are in need of information input.

Furthermore, when the entry field C for the purpose of the visit of this time, symptoms, and the like is selected, the list information of the plurality of symptoms serving as input candidates is displayed. In this way, the patient or the medical staff can input symptoms by simply selecting an applicable symptom from the list described above by a touch operation, making it possible to further reduce the time and effort required to create the medical questionnaire.

Moreover, as the list information of the input candidates described above, a list of symptoms corresponding to a disease that are prevalent in each season, for example, or a list of symptoms corresponding to diseases to which the patient is susceptible to develop based on the medical history of the patient are edited and displayed on a case-by-case basis, thereby making it possible to perform the selection operation of symptoms even more easily and in an even shorter time.

Furthermore, in the embodiment, among the medical interview items entered on the basis of the EMR data or the EHR data DT1 and the PHR data DT2, the patient or the medical staff can selectively modify a medical interview item that needs to be modified due to changes in a symptom or physical condition over time, aging, or the like. Accordingly, it is possible to create more accurate medical questionnaire data while utilizing and yet not being bound by past clinical records in the EMR server MSV or the EHR server HSV and the PHR data DT2 of the mobile information terminal UTi.

Modified Examples (1) In the embodiment, first, the medical questionnaire basic data are created by selecting and pasting necessary data from the EMR or the EHR data DT1 and the PHR data DT2 into, from among each of the medical interview items of the medical questionnaire template data, the personal identification information entry field, the entry field for medical history and the like, and the biological information entry field, and next having the patient or the medical staff fill in the statement data, by manual input, to the entry field of remaining blank medical interview items, that is, items requiring a statement by the patient.

However, the present invention is not limited thereto and, for example, the medical questionnaire basic data may be created by first selecting and pasting the necessary data from the EMR or the EHR data DT1 into, from among each of the medical interview items of the medical questionnaire template data, the personal identification information entry field and the entry field for medical history and the like, and then having the patient or the medical staff fill in the statement data, by manual input, to the entry fields of medical interview items requiring a statement by the patient from among the blank medical interview items. Then, at last, the latest health data, lifestyle data, and the like related to the contents of the statement data of the patient described above may be selected from the PHR data DT2 and pasted into the biological information entry field of the medical questionnaire template data described above.

For example, given that the contents of the statement data of the patient are complaints of fever, sore throat, and the like, a cold such as influenza is suspected, and thus body temperature, blood pressure, and heartbeat are selected from the PHR data DT2 and pasted into the biological information entry field. On the other hand, given that the contents of the statement data of the patient are complaints of abdominal pain, nausea, diarrhea, and the like, food poisoning is suspected, and thus food intake history data indicating the contents of food intake for the past few days are selected and pasted into the biological information entry field in addition to body temperature, blood pressure, and heartbeat.

In this way, because the health data, lifestyle data, and the like related to the contents of the statement data of the patient are selected from the PHR data DT2 and automatically entered into the medical questionnaire data, it is possible to create medical questionnaire data containing necessary and sufficient health information and lifestyle information in accordance with the statement contents of the physical condition of the patient. In particular, when food poisoning is suspected, data indicating the contents of food intake for the past several days are automatically entered into the medical questionnaire data, allowing the medical or healthcare staff to quickly and accurately identify the cause. Further, the patient does not need to recall the contents of the food intake for the past few days, reducing the burden on the patient.

Note that, from among each medical interview item of the medical questionnaire template data, the patient or the medical staff may first fill the statement data into the entry fields of the medical interview items requiring a statement of the patient, and next select and paste data related to the contents of the statement data described above from the EMR or the EHR data DT1 and the PHR data DT2 into the respective fields. In this case, the data related to the contents of the statement data may be selected and pasted from only the EMR or the EHR data DT1 into the fields. As described above, as the data related to the contents of the current statement data of the patient, the most recent biological information of the patient and information of the clinical data of the past such as medical history, or information of the clinical data of the past such as medical history can be automatically selected and entered in the medical questionnaire data.

Further, from among each of the medical interview items of the medical questionnaire template data, when there are a plurality of medical interview items requiring a statement by the patient, preferably a display priority is set in accordance with the importance of these medical interview items, and a display position is controlled so that the medical interview items having greater importance are displayed in positions closer to the top of the medical questionnaire. In general, as the number of medical interview items requiring a statement by the patient increases, entries for later items in the entry order tend to be inaccurate. In contrast, when the medical interview items having high importance are displayed in the beginning of the medical questionnaire as described above, it is more likely that more accurate answers will be entered for the important medical interview items.

As described above, similar to the embodiment, each of the processes described in modified example (1) are realized by executing the program stored in the program memory 11B by the CPU 11A. The configuration of each of the other portions of the medical questionnaire creation assist device NT is the same as that of the embodiment.

(2) The medical questionnaire data may be stored in the EMR server or the EHR server as a portion of the clinical data and, in preparation for such a case, preferably the information indicating the disclosure range of the information is set for each medical interview item of the medical questionnaire data. In this way, when a view request for the medical questionnaire data is generated from a person who wants to view the information other than the patient him or herself, it is possible to restrict the disclosure range of the medical questionnaire data in accordance with a strength of a relationship of the person, who wants to view the information, with the patient.

For example, as the disclosure ranges, the three types of "disclosure permitted to all members", "disclosure permitted to family and physicians only", and "disclosure permitted to only the patient him or herself", for example, are selectively set. Each disclosure range may be collectively set in accordance with rules set in advance for the medical interview items by the EMR server or the EHR server, or set by the patient him or herself or the medical staff such as a physician in the medical interview creation assist terminal NT during the creation of the medical questionnaire, for example. Furthermore, in a state in which the medical questionnaire data are stored on the EMR server or the EHR server, the patient or the medical staff such as a physician may set the disclosure range for each medical interview item by a manual input operation from the mobile information terminals UT1 to UTk or the doctor terminal DT, respectively.

(3) In the embodiment, a case in which a tablet terminal used by a medical institution is provided with the medical questionnaire creation assist function according to this invention and this tablet terminal is used as the medical questionnaire creation assist terminal NT has been described as an example. However, no such limitation is intended and, for example, the medical questionnaire creation assist function may be provided to the EMR server MSV or the EHR server HSV, or may be provided to the mobile information terminals UT1 to UTk possessed by the patients.

When the EMR server MSV or the EHR server HSV is provided with the medical questionnaire creation assist function, the input of the statement information and the display of the medical questionnaire data are performed on a tablet terminal or a stationary personal computer prepared in the medical institution, or on a mobile information terminal possessed by the patient.

In particular, when the mobile information terminal of the patient is provided with the medical questionnaire creation assist function, the patient can create a medical questionnaire before or on the way of a visit to the medical institution, thereby enabling further shortening of outpatient wait time at the medical institution.

(4) In the embodiment, an example is illustrated in which the medical questionnaire data are transmitted from the medical questionnaire creation assist terminal NT to the physician terminal DT. However, no such limitation is intended, and the medical questionnaire data may be transmitted from the medical questionnaire creation assist terminal NT to the EMR server MSV and stored, and the responsible physician may access the EMR server MSV from the physician terminal DT on the basis of the personal identification information PID of the patient to download the medical questionnaire data.

(5) In the embodiment, the medical questionnaire creation assist terminal NT enters, using medical questionnaire template data as a base, the medical interview items pertaining to medical treatment such as medical history on the basis of medical record data such as the EMR data or the EHR data, and the medical interview items pertaining to the biological information of the patient on the basis of biometric data such as the PHR data. However, the medical questionnaire creation assist terminal NT may be configured to enter only one of the medical interview items pertaining to medical treatment and the medical interview items pertaining to biological information, and the other medical interview items may be entered by manual input by the patient him or herself or the medical staff.

In addition, a type and a layout of the medical interview items entered in the medical questionnaire template data, a type and a configuration of the medical questionnaire creation assist device, a procedure and processing contents of the medical questionnaire creation assist process and the like can also be modified in various ways without departing from the gist of this invention.

In short, the invention is not limited to the embodiments described above and can be embodied by modifying the components in an implementation stage in a range without departing from the gist thereof. Further, various inventions can be formed by appropriately combining a plurality of constituent elements disclosed in the embodiment described above. For example, some constituent elements may be omitted from the entire constituent elements shown in the embodiment. Furthermore, the constituent elements of different embodiments may be combined appropriately.

While embodiments of the present invention have been described in detail above, the foregoing description is merely illustrative of the present invention in all respects. Of course, various modifications and variations can be made without departing from the scope of the present invention. Thus, specific configurations in accordance with an embodiment may be adopted as appropriate at the time of carrying out the present invention.

Supplementary Notes

A part or the entirety of each of the embodiments described above can be described as described in the following supplementary notes in addition to the scope of the claims, but the present invention is not limited thereto.

(Supplementary Note 1)
A medical questionnaire creation assist device including a hardware processor (11A) and a memory (11B),
the hardware processor (11A) being configured to execute a program stored in the memory (11B) to
acquire clinical data of the past of a patient on the basis of personal identification information of the patient (1c),
create medical questionnaire basic data of the patient on the basis of medical questionnaire template data including an input region related to each of a plurality of medical interview items that are predetermined and the clinical data being acquired (1a), and add information indicating a generation date and time of each data entered for each of the plurality of medical interview items to the medical questionnaire basic data being created, and cause the display device to display the medical questionnaire basic data with the information indicating the generation date and time being added,
receive input data of statement information regarding a symptom of the patient (1h), and add the input data to the medical questionnaire basic data and create medical questionnaire data of the patient (1a), and
output the medical questionnaire data being created (1d).

(Supplementary Note 2)
A medical questionnaire creation assist method executed by a device including a hardware processor (11A) and a memory (11B) configured to store a program that is executed by the hardware processor (11A), the method including
acquiring clinical data of the past of the patient on the basis of personal identification information of the patient, by the hardware processor (11A) (S14), creating medical questionnaire basic data of the patient on the basis of medical questionnaire template data including an input region related to a plurality of medical interview items that are predetermined and the clinical data being acquired, and adding information indicating a generation date and time of each data entered for each of the plurality of medical interview items to the medical questionnaire basic data being created, and causing the display device to display the medical questionnaire basic data with the information indicating the generation date and time being added, by the hardware processor (11A) (S16),
receiving input data of statement information regarding a symptom of the patient (S19) and adding the input data to the medical questionnaire basic data and creating medical questionnaire data of the patient, by the hardware processor (11A) (S22), and
outputting the medical questionnaire data being created by the hardware processor (11A) (S22).

(Supplementary Note 3)
A medical questionnaire creation assist device including a hardware processor (11A) and a memory (11B),
the hardware processor (11A) being configured to execute a program stored in the memory (11B) to
acquire input data of statement information regarding a symptom of a patient (1h), create medical questionnaire basic data of the patient on the basis of medical questionnaire template data including an input region related to a plurality of medical interview items that are predetermined and the input data being acquired (1a), acquire, on the basis of personal identification information of the patient, at least one of clinical data of the past of the patient and health management data indicating a health state or a lifestyle state of the patient (1b), (1c),
select data related to the statement information, from at least one of the clinical data and the health management data being acquired, and add the data being selected to the medical questionnaire basic data and create medical questionnaire data of the patient (1a), and
output the medical questionnaire data being created (1d).

REFERENCE SIGNS LIST

1 Medical questionnaire creation assist device
2 Mobile information terminal
3 EHR server
4 EMR server
5 Physician terminal
1a Medical questionnaire data creation unit
1b PHR data acquisition unit
1c EHR/EMR data acquisition unit
1d Medical questionnaire data output unit
1e Template storage unit
1f Medical questionnaire data storage unit
1g Display unit
1h Input unit
MS1 to MSn Medical institution
NT Medical questionnaire creation assist terminal
MSV EMR server
HSV EHR server
DT Physician terminal
US1 to USk User
SS1 to SSk Sensing device
UT1 to UTk Mobile information terminal
11 Control unit
12 Data memory
13 Communication I/F
14 Input/Output I/F
15 Display unit
16 Input unit
17 Bus
111 Patient identification information acquisition unit
112 Medical questionnaire data display control unit
113 EHR/EMR data acquisition unit
114 PHR data acquisition unit
115 Medical questionnaire input data acquisition unit
116 Medical questionnaire completed data output unit
117 Medical questionnaire data creation unit
121 Template storage unit
122 Medical questionnaire data storage unit

The invention claimed is:

1. A system comprising:
at least one electronic medical records (EMR) server including a storage and configured to store and manage past clinical data pertaining to a patient for a corresponding medical institution;
an electronic health records (EHR) server including a storage and configured to store and manage past clinical data pertaining to the patient received from the at least one EMR server; and
a medical questionnaire creation assist device configured to communicate with the at least one EMR server and the EHR server, the medical questionnaire creation assist device comprising:
a communication interface configured to communicate with the at least one EMR server and the EHR server; and
a processor configured to:
acquire past clinical data pertaining to the patient from one of the EMR server and the EHR sever via the communication interface on the basis of personal identification information of the patient;
create medical questionnaire basic data of the patient by entering data selected from the clinical data into a first entry field included in medical questionnaire template data, the first entry field corresponding to a part of a plurality of medical interview items that are predetermined, the selected data corresponding the first entry field;
cause the display device to display the created medical questionnaire basic data;
acquire input data of statement information regarding a symptom of the patient, the statement information corresponding to incomplete medical interview items included in the displayed medical questionnaire basic data and add the input data into a second entry field corresponding to the incomplete medical interview items and create completed medical questionnaire data of the patient; and
output the completed medical questionnaire data being created, wherein the processor is further configured to add information indicating a generation date and time of each data entered for each of the plurality of medical interview items to the medical questionnaire basic data being created, and cause the display device to display the medical questionnaire basic data with the information indicating the generation date and time being added,
the processor is further configured to apply, to the medical questionnaire basic data, first marking information highlighting an incomplete medical interview item included in the medical questionnaire basic data being created, and cause the display device to display the medical questionnaire basic data with the first marking information being applied, and
the processor is further configured to detect selection of the incomplete medical interview item included in the medical questionnaire having the first marking applied, read a list information of input candidates from an input candidate storage, and cause the display device to display the list information of input candidates based on the detected selection of the incomplete medical interview item.

2. The medical questionnaire creation assist device according to claim 1, wherein the processor is further configured to:
acquire health management data indicating a health state or a lifestyle state pertaining to the patient, and
create the medical questionnaire basic data of the patient on the basis of the medical questionnaire template data, the clinical data being acquired, and the health management data being acquired.

3. The medical questionnaire creation assist device according to claim 1, wherein
when the generation date and time of each of the data entered for each of the plurality of medical interview items of the data entered in the medical questionnaire basic data being created is earlier than a current time by a period set in advance or longer, the processor is further configured to apply second marking information indicating a degree of reliability to the data, and cause the display device to display the medical questionnaire basic data with the second marking information being applied.

4. The medical questionnaire creation assist device according to claim 1, wherein
the processor is further configured to cause the display device to display list information of input candidates for an incomplete medical interview item included in the medical questionnaire basic data.

5. The medical questionnaire creation assist device according to claim 1, wherein
the processor is further configured to transmit, in response to a medical questionnaire data creation end operation, the medical questionnaire data being created to an external terminal set in advance.

6. A medical questionnaire creation assist method executed in a system including:
at least one electronic medical records (EMR) server including a storage and configured to store and manage past clinical data pertaining to a patient for a corresponding medical institution;
an electronic health records (EHR) server including a storage and configured to store and manage past clinical data pertaining to the patient received from the at least one EMR server; and
a medical questionnaire creation assist device including a communication interface configured to communicate with the at least one EMR server and the EHR server;
a computer, the method comprising:
acquiring past clinical data of the patient from one of the EMR server and the EHR sever via the communication interface of the medical questionnaire creation assist device on the basis of personal identification information of the patient;
creating medical questionnaire basic data of the patient by entering data selected from the clinical data into a first entry field included in medical questionnaire template data, the first entry field corresponding to a part of a plurality of medical interview items that are predetermined, the selected data corresponding to the first entry field;
cause the display device to display the created medical questionnaire basic data;
receiving input data of statement information regarding a symptom of the patient, the statement information corresponding to incomplete medical interview items included in the displayed medical questionnaire basic data and adding the input data into a second entry field corresponding to the incomplete medical interview items and creating completed medical questionnaire data of the patient; and
outputting the completed medical questionnaire data being created, wherein
the creating medical questionnaire basic data includes adding information indicating a generation date and time of each data entered for each of the plurality of medical interview items to the medical questionnaire basic data being created, and causing the display device to display the medical questionnaire basic data with the information indicating the generation date and time being added,
the method further including applying, to the medical questionnaire basic data, first marking information highlighting an incomplete medical interview item included in the medical questionnaire basic data being created, and causing the display device to display the medical questionnaire basic data with the first marking information being applied, and
detecting selection of one of the incomplete medical interview items included in the medical questionnaire having the first marking applied, reading a list information of input candidates from an input candidate storage, and causing the display device to display the list information of input candidates based on the detected selection of the one of the incomplete medical interview items.

7. The medical questionnaire creation assist method according to claim 6, wherein
the creating medical questionnaire basic data includes, when the generation date and time of each of the data entered for each of the plurality of medical interview items of the medical questionnaire basic data being created is earlier than a current time by a period set in advance or longer, applying marking information indicating a degree of reliability to the data, and causing the display device to display the medical questionnaire basic data with the marking information being applied.

8. A non-transitory computer-readable storage medium storing a program executed by at least one processor to perform operations comprising:
acquiring, via a communication interface of a medical questionnaire creation assist device configured to communicate with at least one electronic medical records (EMR) server including a storage and configured to store and manage past clinical data pertaining to a patient for a corresponding medical institution, and an electronic health records (EHR) server including a storage and configured to store and manage past clinical data pertaining to the patient received from the at least one EMR server, past clinical data of a patient from at least one of the at least one an (EMR) server and the (EHR) server on the basis of personal identification information of the patient;
creating medical questionnaire basic data of the patient by entering data selected from the clinical data into a first entry field included in medical questionnaire template data, the first entry field corresponding to a part of a plurality of medical interview items that are predetermined, the selected data corresponding to the first entry field;
cause the display device to display the created medical questionnaire basic data;
receiving input data of statement information regarding a symptom of the patient, the statement information corresponding to incomplete medical interview items included in the displayed medical questionnaire basic data and add the input data into a second entry field corresponding to the incomplete medical interview items and creating completed medical questionnaire data of the patient; and
outputting the completed medical questionnaire data being created, wherein
the creating medical questionnaire basic data includes adding information indicating a generation date and time of each data entered for each of the plurality of medical interview items to the medical questionnaire basic data being created, and causing the display device to display the medical questionnaire basic data with the information indicating the generation date and time being added,
the operations further including applying, to the medical questionnaire basic data, first marking information highlighting an incomplete medical interview item included in the medical questionnaire basic data being created, and causing the display device to display the medical questionnaire basic data with the first marking information being applied, and
detecting selection of the incomplete medical interview item included in the medical questionnaire having the first marking applied, reading a list information of input candidates from an input candidate storage, and causing the display device to display the list information of input candidates based on the detected selection of the incomplete medical interview item.

9. The non-transitory computer-readable storage medium according to claim 8, wherein the operations further comprise acquiring health management data indicating a health state or a lifestyle state pertaining to the patient, and creating the medical questionnaire basic data of the patient on the basis of the medical questionnaire template data, the clinical data being acquired, and the health management data being acquired.

10. The non-transitory computer-readable storage medium according to claim 8, wherein the operations further comprise applying, to the medical questionnaire basic data, first marking information highlighting an incomplete medical interview item included in the medical questionnaire basic data being created, and causing the display device to display the medical questionnaire basic data with the first marking information being applied.

11. The non-transitory computer-readable storage medium according to claim 8, wherein the operations further comprise, when the generation date and time of each of the data entered for each of the plurality of medical interview items of the data entered in the medical questionnaire basic data being created is earlier than a current time by a period set in advance or longer, applying second marking information indicating a degree of reliability to the data, and causing the display device to display the medical questionnaire basic data with the second marking information being applied.

12. The non-transitory computer-readable storage medium according to claim 8, wherein the operations further comprise causing the display device to display list information of input candidates for an incomplete medical interview item included in the medical questionnaire basic data.

13. The non-transitory computer-readable storage medium according to claim 8, wherein the operations further comprise transmitting, in response to a medical questionnaire data creation end operation, the medical questionnaire data being created to an external terminal set in advance.

14. A system comprising:
at least one electronic medical records (EMR) server including a storage and configured to store and manage past clinical data pertaining to a patient for a corresponding medical institution;
an electronic health records (EHR) server including a storage and configured to store and manage past clinical data pertaining to the patient received from the at least one EMR server; and
a medical questionnaire creation assist device, comprising:
a communication interface configured to communicate with the at least one EMR server and the EHR server; and
a processor configured to:
acquire input data of statement information regarding a symptom of a patient, the statement information corresponding to incomplete medical interview items;
create medical questionnaire basic data of the patient by entering data selected from clinical data of the past pertaining to the patient into a first entry field included in medical questionnaire template data, the first entry field corresponding to a part of a plurality of medical interview items that are predetermined, the selected data corresponding to the first entry field;
acquire, from one of the EMR server and the EHR sever via the communication interface of the medical questionnaire creation assist device, on the basis of personal identification information of the patient, at least one of the clinical data or health management data indicating a health or lifestyle state pertaining to the patient;
select, from the at least one of the clinical data or the health management data being acquired, data related to the statement information, and add the data being selected into a second entry field corresponding to the incomplete medical interview items included in the medical questionnaire basic data, and create completed medical questionnaire data of the patient; and
output the completed medical questionnaire data being created,
wherein the processor is further configured to apply, to the medical questionnaire basic data, first marking information highlighting an incomplete medical interview item included in the medical questionnaire basic data being created, and cause the display device to display the medical questionnaire basic data with the first marking information being applied, and
wherein the processor is further configured to detect selection of the incomplete medical interview item included in the medical questionnaire having the first marking applied, read a list information of input candidates from an input candidate storage, and cause the display device to display the list information of input candidates based on the detected selection of the incomplete medical interview item.

15. A non-transitory computer-readable storage medium storing a program for causing the processor provided to the medical questionnaire creation assist device according to claim 14 to execute processing in the medical questionnaire creation assist device.

16. A medical questionnaire creation assist method in a system including:
at least one electronic medical records (EMR) server including a storage and configured to store and manage past clinical data pertaining to a patient for a corresponding medical institution;
an electronic health records (EHR) server including a storage and configured to store and manage past clinical data pertaining to the patient received from the at least one EMR server; and
a medical questionnaire creation assist device including a communication interface configured to communicate with the at least one EMR server and the EHR server, the method comprising:
acquiring input data of statement information regarding a symptom of a patient, the statement information corresponding to incomplete medical interview items;
creating medical questionnaire basic data of the patient by entering data selected from clinical data of the past pertaining to the patient into a first entry field included in medical questionnaire template data, the first entry field corresponding to a part of a plurality of medical interview items that are predetermined, the selected data corresponding to the first entry field;
acquiring, from one of the EMR server and the EHR sever via the communication interface of the medical questionnaire creation assist device, on the basis of personal identification information of the patient, at least one of the clinical data or health management data indicating a health or lifestyle state pertaining to the patient;
selecting, from the at least one of the clinical data or the health management data being acquired, data related to the statement information, and adding the data being selected into a second entry field corresponding to the incomplete medical interview items included in the medical questionnaire basic data, and creating completed medical questionnaire data of the patient; and outputting the completed medical questionnaire data being created, wherein the method further includes applying, to the medical questionnaire basic data, first marking information highlighting an incomplete medical interview item included in the medical questionnaire basic data being created, and causing the display device to display the medical questionnaire basic data with the first marking information being applied, and detecting selection of the incomplete medical interview item included in the medical questionnaire having the first marking applied, reading a list information of input candidates from an input candidate storage, and causing the display device to display the list information of input candidates based on the detected selection of the incomplete medical interview item.

* * * * *